US009139737B1

(12) United States Patent  
Shah et al.

(10) Patent No.: US 9,139,737 B1  
(45) Date of Patent: Sep. 22, 2015

(54) MULTIFUNCTIONAL COATED POWDERS AND HIGH SOLIDS DISPERSIONS

(75) Inventors: Kushal D. Shah, Schiller Park, IL (US); Harry W. Sarkas, Plainfield, IL (US); Patrick G. Murray, Yorkville, IL (US)

(73) Assignee: Nanophase Technologies Corporation, Romeoville, IL (US)

( * ) Notice: Subject to any disclaimer, the term of this patent is extended or adjusted under 35 U.S.C. 154(b) by 508 days.

(21) Appl. No.: 13/301,628

(22) Filed: Nov. 21, 2011

(51) Int. Cl.  
*C09C 1/36* (2006.01)  
*C09C 3/12* (2006.01)

(52) U.S. Cl.  
CPC ............... *C09C 1/3684* (2013.01); *C09C 3/12* (2013.01); *C01P 2004/80* (2013.01); *C01P 2006/22* (2013.01); *Y10T 428/2995* (2015.01); *Y10T 428/2998* (2015.01)

(58) Field of Classification Search  
CPC .......... Y10T 428/2995; Y10T 428/2998; C09C 3/12; C09C 1/3684; C01P 2004/80; C01P 2006/22  
See application file for complete search history.

(56) References Cited

U.S. PATENT DOCUMENTS

| | | |
|---|---|---|
| 2,885,366 A | 5/1959 | Iler |
| 2,938,009 A | 5/1960 | Lucas |
| 3,024,126 A | 3/1962 | Brown |
| 3,437,502 A | 4/1969 | Werner |
| 3,562,153 A | 2/1971 | Tully et al. |
| 3,635,743 A | 1/1972 | Smith |
| 3,647,742 A | 3/1972 | Stevens, Jr. |
| 3,649,588 A | 3/1972 | Kennedy-Skipton |
| 3,671,484 A | 6/1972 | Cooper et al. |
| 3,816,152 A | 6/1974 | Yates |
| 3,849,152 A | 11/1974 | Mimeault |
| 3,905,936 A | 9/1975 | Hawthorne |
| 3,920,865 A | 11/1975 | Laufer et al. |
| 3,948,676 A | 4/1976 | Laufer |
| 4,061,503 A | 12/1977 | Berger et al. |
| 4,068,024 A | 1/1978 | Laufer |
| 4,141,751 A | 2/1979 | Moreland |
| 4,151,154 A | 4/1979 | Berger |
| 4,233,366 A | 11/1980 | Sample, Jr. et al. |
| 4,243,692 A | 1/1981 | Scholze et al. |
| 4,271,234 A | 6/1981 | Schonafinger et al. |
| 4,454,288 A | 6/1984 | Lee et al. |
| 4,556,175 A | 12/1985 | Motoyama et al. |
| 4,574,082 A | 3/1986 | Tietjen et al. |
| 4,644,077 A | 2/1987 | Gupta |
| 4,781,942 A | 11/1988 | Leyden et al. |
| 4,818,614 A | 4/1989 | Fukui et al. |
| 4,845,054 A | 7/1989 | Mitchener |
| 4,877,604 A | 10/1989 | Schlossman |
| 4,882,225 A | 11/1989 | Fukui et al. |
| 4,927,464 A | 5/1990 | Cowie |
| 5,035,803 A | 7/1991 | Cohen |
| 5,063,254 A | 11/1991 | Nakos |
| 5,068,056 A | 11/1991 | Robb |
| 5,070,175 A | 12/1991 | Tsumura et al. |
| 5,143,722 A | 9/1992 | Hollenberg et al. |
| 5,274,064 A | 12/1993 | Sarkar |
| 5,277,888 A | 1/1994 | Baron et al. |
| 5,310,578 A | 5/1994 | Thurn-Muller et al. |
| 5,328,683 A | 7/1994 | Harashima |
| 5,348,760 A | 9/1994 | Parker et al. |
| 5,411,761 A | 5/1995 | Inokuchi et al. |
| 5,440,001 A | 8/1995 | Griswold et al. |
| 5,486,631 A | 1/1996 | Mitchnick et al. |
| 5,536,492 A | 7/1996 | Mitchnick et al. |
| 5,562,897 A | 10/1996 | Mitchnick et al. |
| 5,565,591 A | 10/1996 | Mitchnick et al. |
| 5,607,994 A | 3/1997 | Tooley et al. |
| 5,631,310 A | 5/1997 | Tooley et al. |
| 5,674,624 A | 10/1997 | Miyazaki et al. |
| 5,679,402 A | 10/1997 | Lee |
| 5,718,907 A | 2/1998 | Labarre |
| 5,756,788 A | 5/1998 | Mitchnick et al. |
| 5,843,525 A | 12/1998 | Shibasaki et al. |
| 5,868,959 A | 2/1999 | Mayo et al. |
| 5,959,004 A | 9/1999 | Tooley et al. |
| 5,993,967 A | 11/1999 | Brotzman, Jr. et al. |
| 6,022,404 A | 2/2000 | Ettlinger et al. |
| 6,033,781 A | 3/2000 | Brotzman, Jr. et al. |
| 6,045,650 A | 4/2000 | Mitchnick et al. |
| 6,086,668 A | 7/2000 | Farneth et al. |
| 6,177,414 B1 | 1/2001 | Tomalia et al. |
| 6,214,106 B1 | 4/2001 | Weber et al. |

(Continued)

FOREIGN PATENT DOCUMENTS

| | | |
|---|---|---|
| CA | 2010790 | 9/1990 |
| DE | 2828659 | 2/1979 |

(Continued)

OTHER PUBLICATIONS

Jacobsen, A.E. et al., "Titanium dioxide pigments: Correlation between photochemical reactivity and chalking", Industrial and Engineering Chemistry, vol. 41, No. 3, pp. 523-526, (1949).

Brinker, et al., "Sol-Gel Science, The physics and chemistry of sol-gel processing", Academic press, chapters 3 and 4, pp. 97-301, (1990).

Supplementary European Search Report in European Patent Application No. 05760444.9-2011, dated May 15, 2009.

International Search Report dated Dec. 5, 2006 for PCT Application No. PCT/US05/10669.

Kinsley, Jr., G.R. "Properly purge and inert storage vessels", Chemical Engineering Progress, vol. 97, No. 2, pp. 57-61, (2001).

Baldyga, J. et al., "Effects of fluid motion and mixing on particle agglomeration and coating during precipitation", Chemical Engineering Science, vol. 60, issues 8-9, pp. 2167-2178, (2005).

(Continued)

*Primary Examiner* — Abigail Fisher  
*Assistant Examiner* — Daniel L Branson  
(74) *Attorney, Agent, or Firm* — Evan Law Group LLC

(57) ABSTRACT

A coated powder comprises (a) nanoparticles, and (b) a coating, on the surface of the nanoparticles. The coating comprises (1) silica moieties, (2) organo oxysilane moieties selected from the group consisting of mono-organo oxysilane moieties, bi-organo oxysilane moieties and tri-organo oxysilane moieties, and (3) poly(dialkyl)siloxane moieties.

20 Claims, No Drawings

(56) References Cited

U.S. PATENT DOCUMENTS

| | | | |
|---|---|---|---|
| 6,500,415 | B2 | 12/2002 | Ishii et al. |
| 6,599,631 | B2 | 7/2003 | Kambe et al. |
| 7,052,777 | B2 | 5/2006 | Brotzman, Jr. et al. |
| 7,182,938 | B2 | 2/2007 | Andre et al. |
| 7,303,819 | B2 | 12/2007 | Brotzman, Jr. |
| 7,438,836 | B2 | 10/2008 | Michael et al. |
| 2005/0222325 | A1 | 10/2005 | Brotzman, Jr. |
| 2005/0255057 | A1 | 11/2005 | Andre et al. |
| 2006/0167138 | A1 | 7/2006 | Ishii et al. |
| 2006/0210495 | A1 | 9/2006 | Meyer et al. |
| 2008/0057130 | A1 | 3/2008 | Brotzman, Jr. |

FOREIGN PATENT DOCUMENTS

| | | |
|---|---|---|
| EP | 0 389 138 | 9/1990 |
| EP | 0 558 032 | 9/1993 |
| EP | 0 665 004 | 8/1995 |
| EP | 0 761 774 | 7/2003 |
| GB | 785393 | 10/1957 |
| GB | 825404 | 12/1959 |
| GB | 2217987 | 11/1989 |
| JP | 62-016408 | 1/1987 |
| JP | 03-081209 | 4/1991 |
| JP | 4-178428 | 6/1992 |
| JP | 5-221640 | 8/1993 |
| JP | 5-306338 | 11/1993 |
| JP | 06-087714 | 3/1994 |
| JP | 6-279589 | 10/1994 |
| JP | 7-157562 | 6/1995 |
| JP | 7-165921 | 6/1995 |
| WO | 90/06103 | 6/1990 |
| WO | 90/09777 | 9/1990 |
| WO | 95/23192 | 8/1995 |
| WO | 97/38041 | 10/1997 |
| WO | 2005/098910 | 10/2005 |
| WO | 2009/131910 | 10/2009 |

OTHER PUBLICATIONS

Solomon, D.H. et al., "Titania Pigments" "Surface modification of pigments and fillers" "Organic reactions catalyzed by mineral surkefaces", chemistry of Pigments and Fillers, John Wiley & Sons, (1983).
International Search Report dated Aug. 4, 1997 for PCT Application No. PCT/US97/05179.
International Cosmetic Ingredient Dictionary, 5th edition, Published by The Cosmetic, Toiletry, and Fragrance Association, vol. 1, p. 401, (1993).
International Cosmetic Ingredient Dictionary, 5th edition, Published by The Cosmetic, Toiletry, and Fragrance Association, vol. 1, pp. 649-650, (1993).
International Cosmetic Ingredient Dictionary, 5th edition, Published by The Cosmetic, Toiletry, and Fragrance Association, vol. 2, p. 924, (1993).
Kingery, W.D. et al., "Introduction to Ceramics", 2nd Edition, John Wiley & Sons, pp. 3, 16-20, (1976).
Rompp Lexikon Chemie, 10, Auflage, pp. 4564-4565, (1999).
Rompp Lexikon Chemie, 10, Auflage, pp. 5076, (1999).
Odian, G. "Principles of Polymerization", 2nd Edition, John Wiley & Sons, pp. 238-239 400-401 424-425, (1981).
Billmeyer, Jr., F.W. Textbook of Polymer Science, Interscience Publishers, pp. 332-337, (1962).
Jastrzebski, Z.D. "Ceramics and Related Materials", Nature and Properties of Engineering Materials, John Wiley & Sons, Inc. p. 281, (1959).
Billmeyer, Jr., F.W. Textbook of Polymer Science, Interscience Publishers, p. 350, (1971).
Odian, G. "Principles of Polymerization", 2nd Edition, John Wiley & Sons, pp. 429-430, (1981).
Flory, P.J. "Nonlinearity in the macro-structure of vinyl polymers", Principles of Polymer Chemistry, Cornell University Press, Chapter III and Chapter VI, section 4, pp. 69-105, 256-262, (1971).
Meakin, P. "Models for colloidal aggregation", Annual Reviews Physical Chemistry, vol. 39, pp. 237-267, (1988).
Brinker, et al., "Sol-Gel Science, the physics and chemistry of sol-gel processing", Academic press, chapters 1, pp. 1-8, (1990).
Kingery, W.D. et al., "Introduction to Ceramics", 2nd Edition, John Wiley & Sons, pp. 61-71, (1976).

MULTIFUNCTIONAL COATED POWDERS AND HIGH SOLIDS DISPERSIONS

BACKGROUND

Particles are added to enhance and modify the properties of many different types of compositions and products. Examples include ultra-violet (UV) light absorbing particles, pigments, colorants, fillers, matting agents, optical diffusing particles, abrasion resistant particles, viscosity modifiers, magnetic particles and reflective particles. Especially in the case of nanoparticles, a very small weight percent (wt %) of particles added to the composition or product can dramatically affect properties. In order to be effective at such low weight percents, the particles must remain dispersed and chemically stable, during both the production and use of the composition or product. These problems are exacerbated as the dimensions of the particles are reduced because of the increase in total surface area, on a weight basis.

Chemical instability can result from reaction of the particles with other reagents, as well as with agents present in the environment, during any of the phases of the composition or product, such as manufacture, storage and use. Chemical instability may be exacerbated by environmental factors, such as exposure to visible and UV light, or exposure to elevated temperatures. Particle aggregation or poor dispersability is often the result of incompatibility of the particle surface with fluid components, especially incompatible hydrophobic/hydrophilic and electrostatic interactions with solvents or other particulate additives. Particle aggregation or poor dispersability may also be exacerbated by environmental factors, such as exposure to elevated temperatures, or long storage times. For large scale transport and ease of handling, it is often desirable to prepare liquid dispersions with high weight loading of the nanoparticles.

Particles comprising oxides are particularly suitable as additives, especially particles containing zinc oxides, titanium oxides, silicon oxides, aluminum oxides, iron oxides and/or rare-earth metal oxides. These oxides are thermodynamically stable, are typically unable to react with environmentally ubiquitous oxygen, and tend to be less reactive with water than many other oxides and non-oxide materials. These oxide materials have been used as pigments and abrasives for centuries. Nanoparticles consisting of certain metal oxides, most notably titanium oxides, are particularly interesting for use in coating compositions, because they are usually colorless and transparent to visible light, and provide protection against exposure to UV light; however they tend to have poor photostability, caused by the photocatalytic behavior of these oxides. In cosmetic preparations, poor photostability often manifests as a color change and is not acceptable for commercial topical skin products. Poor photostability also interferes with use in paints or other product coatings, resulting in reactivity and "chalking out".

In order to improve dispersability in non-aqueous fluids, particles have been coated or surface treated with hydrophobic reagents. Coatings and surface treatments have also been used to enhance chemical stability, including the photostability of titanium and other oxides.

T-Cote 031 is a microfine titania (titanium oxide) with a mean particle size of less than 200 nm which has been treated with dimethicone (poly(dimethylsiloxane)) on the particle surface. The hydrophobic dimethicone surface treatment provides compatibility with non-aqueous oils that serve as liquid carriers in a variety of products. While this nanoparticle material is used to produce dispersions at high weight loading, a major deficiency in photostability prevents its use in dispersions intended for commercial use. The performance of T-Cote 031 indicates that a simple dimethicone treatment is not sufficient to enhance photostability, as the photostability of this material is nearly indistinguishable from uncoated microfine titania.

Aeroxide T805 is a fumed titanium dioxide powder which has been treated to form octyl silane $(H(CH_2)_8Si(O)_3)$ moieties on the particle surface. Presumably, the octyl silane coating is applied by reacting the particle surface with a trifunctional alkoxy octylsilane such as triethoxy octylsilane. While this treatment does not render the titania surface completely inert, it is sufficiently chemically stable for some commercial applications. Aeroxide T805 is sufficiently photostable for use as an additive in a cosmetic preparation, and is currently used in several topical human sunscreens. High solids dispersions are highly desirable in sunscreen formulations since they enable high SPF (Sun Protection Factor) values to be achieved while introducing a minimal amount of carrier fluid. However, difficulty is encountered when high solids dispersions are formulated; typically a paste is formed. These high solids dispersions are commercially available, but due to high viscosity, they are difficult to mix with other reagents and are prone to waste since it is difficult to remove all of the material from the storage container.

SUMMARY

In a first aspect, the present invention is a coated powder comprising (a) nanoparticles, and (b) a coating, on the surface of the nanoparticles. The coating comprises (1) silica moieties, (2) organo oxysilane moieties selected from the group consisting of mono-organo oxysilane moieties, bi-organo oxysilane moieties and tri-organo oxysilane moieties, and (3) poly(dialkyl)siloxane moieties.

In a second aspect, the present invention is a process for producing a coated powder, comprising coating nanoparticles with a polymer. The coating is prepared by polymerizing a composition comprising (i) the nanoparticles, (ii) a first alkoxy silane selected from the group consisting of a tetra-alkoxy silane, a poly(tetra-alkoxy silane), and mixtures thereof, (iii) an organo alkoxysilane selected from the group consisting of mono-organo alkoxysilane, bi-organo alkoxysilane, tri-organo alkoxysilane, and mixtures thereof, and (iv) a second alkoxy silane selected from the group consisting of a poly(dialkyl)siloxane, and mixtures thereof.

In a third aspect, the present invention is a dispersion, comprising the coated powders and a liquid carrier.

In a fourth aspect, the present invention is a composition comprising the coated powders and a resin.

In a fifth aspect, the present invention is a composition comprising the coated powders. The composition is a paint, stain, coating, or ink.

In a sixth aspect, the present invention is a method of protecting skin from light, comprising coating skin with a composition comprising the coated powders.

DEFINITIONS

The term "nanoparticle" means a particle having a particle size of at most 999 nm. Preferably, a nanoparticle has a particle size of 10 nm to 500 nm.

The term "particle size" means the average diameter of the image of the particle as viewed by electron microscopy, unless otherwise stated. The term "average particle size" means the average of the particle sizes of a collection of particles.

"High solids content" or "high weight loading" means that the composition referred to has at least 50 wt. % solid particle.

"Alkyl" (or alkyl- or alk-) refers to a substituted or unsubstituted, straight, branched or cyclic hydrocarbon chain, preferably containing of from 1 to 20 carbon atoms. More preferred alkyl groups are lower alkyl groups, for example, alkyl groups containing from 1 to 10 carbon atoms. Preferred cycloalkyls have 3 to 10, preferably 3-6, carbon atoms in their ring structure. Suitable examples of unsubstituted alkyl groups include methyl, ethyl, propyl, isopropyl, cyclopropyl, butyl, iso-butyl, tert-butyl, sec-butyl, cyclobutyl, pentyl, cyclopentyl, hexyl, and cyclohexyl.

"Alkenyl" refers to a substituted or unsubstituted, straight, branched or cyclic, unsaturated hydrocarbon chain that contains at least one double bond, and preferably having 2 to 20, more preferably 2 to 6, carbon atoms. Exemplary unsubstituted alkenyl groups include ethenyl (or vinyl) (—CH=CH$_2$), 1-propenyl, 2-propenyl (or allyl) (—CH$_2$—CH=CH$_2$), 1,3-butadienyl (—CH=CHCH=CH$_2$), 1-butenyl (—CH=CHCH$_2$CH$_3$), hexenyl, pentenyl, and 1,3,5-hexatrienyl. Preferred cycloalkenyl groups contain 5 to 8 carbon atoms and at least one double bond. Examples of cycloalkenyl groups include cyclohexadienyl, cyclohexenyl, cyclopentenyl, cycloheptenyl, cyclooctenyl, cyclohexadienyl, cycloheptadienyl, and cyclooctatrienyl.

"Alkynyl" refers to a substituted or unsubstituted, straight, branched or cyclic unsaturated hydrocarbon chain containing at least one triple bond, and preferably having 2 to 20, more preferably 2 to 6, carbon atoms.

"Aryl" refers to any aromatic carbocyclic or heteroaromatic group, preferably having 3 to 10 carbon atoms. The aryl group can be cyclic (such as phenyl (or Ph)) or polycyclic (such as naphthyl) and can be unsubstituted or substituted. Preferred aryl groups include phenyl, naphthyl, furyl, thienyl, pyridyl, indolyl, quinolinyl or isoquinolinyl.

"Heterocyclic radical" refers to a stable, saturated, partially unsaturated, or aromatic ring, preferably containing 5 to 10, more preferably 5 or 6, atoms. The ring can be substituted 1 or more times (preferably 1, 2, 3, 4 or 5 times) with substituent(s). The ring can be mono-, bi- or polycyclic. The heterocyclic group consists of carbon atoms and 1 to 3 heteroatoms independently selected from the group consisting of nitrogen, oxygen, and sulfur. The heteroatoms can be protected or unprotected. Examples of useful heterocyclic groups include substituted or unsubstituted acridine, benzathiazoline, benzimidazole, benzofuran, benzothiophene, benzthiazole, benzothiophenyl, carbazole, cinnoline, furan, imidazole, 1H-indazole, indole, isoindole, isoquinoline, isothiazole, morpholine, oxazole, phenazine, phenothiazine, phenoxazine, phthalazine, piperazine, pteridine, purine, pyrazine, pyrazole, pyridazine, pyridine, pyrimidine, pyrrole, quinazoline, quinoline, quinoxaline, thiazole, 1,3,4-thiadiazole, thiophene, 1,3,5-triazines, and triazole.

"Substituted" means that the moiety contains at least one, preferably 1-3 substituent(s). Suitable substituents include hydrogen (H) and hydroxyl (—OH), amino (—NH2), oxy (-0-), carbonyl (—CO—), thiol, alkyl, alkenyl, alkynyl, alkoxy, halo, nitrile, nitro, aryl, and heterocyclic groups.

Photostability is measured using the following photostability test, which was adapted from photochemical activity tests well known in the titania pigment and paint industry modified so that uncoated and coated (hydrophobic) powders could be evaluated in a single matrix. See *"Titanium Dioxide Pigments: Correlation between Photochemical Reactivity and Chalking"* from the National Lead Company 1949 (Industrial and Engineering Chemistry Volume 41 Number 3). The photooxidizable matrix used in the present photostability test is a 3:1 mixture (by weight) of white petrolatum (White Petrolatum USP 100%) and glycerol (Glycerine USP 96% Dow Chemical). The petrolatum and glycerol are first mixed until a homogeneous matrix mixture is obtained. This matrix mixture is then thoroughly blended with one part (by weight) of the powder to be tested, to form the test mixture. The final ratio is 3 parts white petrolatum:1 part glycerol:1 part powder by weight. In the case of dispersions of powders the procedure is modified by using 1 part (by weight) of a 50 wt % powder dispersion in ethylhexyl benzoate (Finsolv® EB, Innospec, CAS Number 5444-75-7) blended with 0.5 parts glycerine and 3.5 parts white petrolatum to form the test mixture (so that the ratio of powder:glycerol by weight is 1:1). The test mixtures are then placed in a 1 inch diameter×2 mm deep stainless steel well and sealed from the atmosphere with a 2 mm quartz cover. The test mixtures are then exposed to UV light in a Q-Labs QUV weatherometer using UVB bulbs at 0.35 Wm$^{-2}$s$^{-1}$ at a constant temperature of 50° C. Samples are exposed in the weatherometer for set times of 5 minutes, 10 minutes, 15 minutes and/or 30 minutes; if no time is specified then only a 15 minute exposure is used. Color measurements are then made on each test mixture by colorimetry on the exposed face through the quartz cover. The colorimeter used in the present studies was a Data Color-International Spectraflash SF3000 Colorimeter, although equivalent instruments may be employed. Photostability may be expressed as the total color change ($\Delta E$ in LAB* color space) for a stated UV exposure time. Both the zero time absolute color of each test mixture and a standard factory white tile are used as standards. A powder is not considered to be photostable in application if the photostability test results in the appearance of a blue color with an accompanying $\Delta E$ value greater than 8 after 15 minutes of UV exposure time.

For compositions other than TiO$_2$ where no direct color change necessarily results from a lack of photostability, the test described previously may be modified to include a suitable indicator dye. Suitable indicator dyes are those that can be dissolved in at least one of the components of the carrier matrix, display inherent photostability in the absence of radical generating species, and can be photo-bleached via reaction with radicals generated as a result of photo-excitation of the inorganic species to be tested. Azo dyes are typically well suited for this test with the preferred dye being Disodium 6-hydroxy-5-[(4-sulfophenyl)azo]-2-naphthalenesulfononate (Sunset Yellow, Orange Yellow S; FD&C Yellow 6; C.I. 15985; E110; CAS Number 2783-94-0). Photostability following UV exposure is indicated by the persistence of the orange color due to the absorption band of the dye at 480 nm. As in the test previously described, color is monitored via colorimetry. In addition to the azo dyes, the dye DPPH (di (phenyl)-(2,4,6-trinitrophenyl)iminoazanium, 2,2-diphenyl-1-picrylhydrazyl; 1,1-diphenyl-2-picrylhydrazyl radical; 2,2-diphenyl-1-(2,4,6-trinitrophenyl)hydrazyl; diphenylpicrylhydrazyl; CAS Number 1898-66-4) can also be used in this test at the same loading level. In this case, photostability following UV exposure is indicated by the persistence of the purple color due to the absorption band of the dye at 520 nm.

Chemical reactivity is measured using the following chemical reactivity test. A 20 dram glass vial is filled with 4.5 g of a stock solution of 5% n-propyl gallate (propyl 3,4,5-trihydroxybenzoate, Aldrich) in isopropyl alcohol. One half of a gram of the powder to be evaluated is added to the glass vial. The glass vial is then agitated, such as by being placed in a bath sonicator for 30 seconds. The mixture is allowed to stand for 30 minutes. The sample is then gently mixed using a pipette and transferred to a cuvette (polycarbonate, polystyrene, or glass) having a path length of 1 cm. The total color change (ΔE) is then measured against a factory white color standard using a Data Color-International Spectraflash SF3000 Colorimeter. Chemical reactivity is expressed as the total color change (ΔE). A powder is considered to be chemically reactive in application if the chemical reactivity test results in the appearance of a tan color with an accompanying ΔE value greater than 20.

Hydrophobicity is measured using the following hydrophobicity test (this test is a visible water floatation test commonly used in the cosmetics industry, and is described in U.S. Pat. No. 4,454,288). Approximately 30 mL of deionized water is placed into a glass jar. Approximately 3.0 g±0.30 g of the powder to be tested is added into the glass jar. The glass jar is tightly sealed, and the sample is swirled around 4 to 5 times and vigorously shaken 4 to 5 times, so that intimate contact between the water and the powder is achieved. The powder is considered to be hydrophobic if the powder is buoyant (floating on the surface of the water) and water is clear after 15 minutes. The sample is marginally hydrophobic if the powder is not buoyant but the water is clear after 15 minutes, or if the powder is buoyant but the water is not clear after 15 minutes.

The fluidity of dispersions of powders is measured using the following run-off distance test. Dispersions are produced at 50% solids in ethylhexyl benzoate (Finsolv® EB, Innospec). Three drops (75 mg) of the dispersion from a pipette are placed onto a clean glass plate substrate while the surface is in a horizontal position. The glass substrate is then held upright for 120 seconds at an angle of 90 degrees to allow the dispersion to flow. The fluidity of the dispersion is expressed as the distance the dispersion flows from the origin. (This test was only used during initial screening; a measured run-off distance of 164±10 mm (reported as standard error) from the origin corresponds to a viscosity of 145±25 cP (reported as standard error) at a shear rate of 20 $s^{-1}$.). A coated powder is considered to produce a pourable dispersion if at 50% solids in an ethylhexyl benzoate dispersion it shows a run-off distance exceeding 100 mm.

The viscosity of dispersions of powders is measured using the following viscosity test. Dispersions of the powders are prepared in capric/caprylic triglycerides (ALDO® MCT Special KFG, Lonza, CAS Number 73398-61-5), ethylhexyl benzoate (Finsolv® EB, Innospec), and linear alkyl benzoate (Finsolv® TN $C_{12-15}$ Alkyl Benzoate CAS No.: 68411-27-8) at 50 wt % solids, unless otherwise specified. Viscosity is measured for each dispersion using a Brookfield DVIII+ Ultra Rheometer with a CP52 spindle at 25° C. Measurements are made at shear rates ranging from 0.1 $s^{-1}$ to 100 $s^{-1}$.

DETAILED DESCRIPTION

Coated powders of $TiO_2$ and other selected metal oxides would be desirable for use in UV protective topical skin compositions, and other UV protective coatings. However, in order to be commercially desirable, such coated powders need to be (a) photostable, so that they do not significantly change color during exposure to UV light; (b) not chemically reactive, so that they do not react with or discolor compositions during storage; and (c) may be formed into high weight loading dispersions which allow for high SPF values with minimal introduction of carrier fluid and for cost efficient transport and storage, but which have a viscosity low enough for easy handling and mixing when preparing consumer compositions. Dispersions of T-Cote 031, have a manageable viscosity at high weight loading, but have undesirable photostability and chemical reactivity. Aeroxide T805 is photostable and not chemically reactive, but high weight loading dispersions of this coated powder are too viscous for easy handling and mixing.

In an effort to develop a polymer coating which would provide both the photostability and low chemical reactivity observed with powders coated with trifunctional alkoxy octylsilane (such as Aeroxide T805), and the low viscosity high weight loading dispersions observed with powders coated with poly(dimethylsiloxane) (such as T-Cote 031), combinations of these two surface treatments were used to prepare coated powders of $TiO_2$. As expected, increasing the proportion of trifunctional alkoxy octylsilane used to prepare the coating increased the photostability and decreased the chemical reactivity; likewise, increasing the proportion of poly(dimethylsiloxane) used to prepare the coating reduced the viscosity of high weight loading dispersions. However, it was not possible to increase the photostability and reduce the chemical reactivity, and at the same time achieve a sufficiently low viscosity of high weight loading dispersions. Therefore, a new approach was needed to achieve a coated powder having commercially desirable photostability and chemical reactivity, as well as a high weight loading dispersion with low viscosity.

The photostability of Aeroxide T805 is thought to result from the formation of inorganic caps (such as $SiO_3$ moieties) on the particle surface by reaction of the alkoxy groups of the trialkoxy alkylsilane. Therefore, substitution of the trifunctional alkoxy octylsilane with tetraethoxy silane would be expected to improve the photostability and decrease chemical reactivity because of the possibility of an increase in inorganic cap formation on the particle surface as well as an increased self-polymerization of the tetraethoxy silane and resulting increased thickness of the inorganic caps at the particle surface. This combination yielded a powder which displayed good photostability and chemical reactivity, but surprisingly, the dispersions were too viscous. Again, a new approach was need to achieve a coated powder having commercially desirable photostability and chemical reactivity, as well as a high weight loading dispersion with low viscosity.

The present invention makes use of the discovery of coated powders which are hydrophobic and photostable. The powder particles are nanoparticles coated with a polymer, prepared by polymerizing a composition containing the nanoparticles and at least three components: (A) a first alkoxy silane selected from the group consisting of a tetra-alkoxy silane, a poly(tetra-alkoxy silane), and mixtures thereof, (B) an organo alkoxysilane selected from the group consisting of mono-organo alkoxysilane, bi-organo alkoxysilane, tri-organo alkoxysilane, and mixtures thereof, and (C) a second alkoxy silane selected from the group consisting of a poly(dialkyl) siloxane, and mixtures thereof. The coating formed contains moieties corresponding with each of the three components: (A) silica moieties, (B) organo oxysilane moieties selected from the group consisting of mono-organo oxysilane moieties, bi-organo oxysilane moieties and tri-organo oxysilane moieties, and (C) poly(dialkyl)siloxane moieties. The coated nanoparticles can be used to form dispersions in cosmetically acceptable fluids which have high solids and low viscosity. The dispersion may be used to prepare cosmetic compositions for application to the skin, such as composition for protecting skin from UV radiation (for example, sunscreens). Materials considered to be cosmetically acceptable are those which are INCI (International Nomenclature of Cosmetic Ingredients) listed. Examples of cosmetically acceptable fluids are ethylhexyl benzoate (EB), linear alkyl benzoate (LAB), caprylic/capric triglyceride (CTG), natural product oils, and a variety of silicone fluids. Natural product oils are oils derived from seeds, beans, fruits, flowers, peels, leaves, and the like, including their derivatives. Examples of natural product oils are olive oil and soybean oil.

The nanoparticles preferably comprise a metal oxide, for example zinc oxide, titanium oxide, silicon oxide, aluminum oxide, iron oxide, bismuth oxide, cerium oxide, rare-earth oxides, infrared light absorbing binary and ternary mixed metal oxides and mixtures thereof. Examples include ZnO, $TiO_2$, $SiO_2$, $Al_2O_3$, $Fe_2O_3$, $CeO_2$, zirconium-cerium oxides, mixed zirconium-rare earth oxides containing cerium, aluminosilicates (including amorphous aluminosilicate, crystalline aluminosilicates, and pumice) and other silicates, aluminum oxides include alumina, aluminosilicates, magnesium aluminum oxides (for example, spinel), zinc oxide doped with trivalent metal cations (including aluminum-doped ZnO), antimony-tin oxide (ATO), indium-tin oxide (ITO) and doped tungsten oxides. Metals, other ceramic compositions including carbides and nitrides and mixtures thereof, as well as mixtures with oxides, may also be used.

The nanoparticles have a particle size of at most 999 nm, including a particle size of at most 100, 200, and 500 nm, more preferably a particle size of 10 nm to 500 nm, most preferably a particle size of 15 nm to 250 nm, such as 20, 30, 40, 50, 60, 70, 80, 90, and 100 nm. Preferably, the nanoparticles have an average particle size of at most 999 nm, including an average particle size of at most 100, 200, and 500 nm, more preferably an average particle size of 10 nm to 500 nm, most preferably an average particle size of 15 nm to 250 nm, such as 20, 30, 40, 50, 60, 70, 80, 90, and 100 nm.

The nanoparticles may be coated by polymerizing the composition, preferably without solvents and with at least some of the composition in the gas phase. The composition includes (A) a first alkoxy silane selected from the group consisting of a tetra-alkoxy silane, a poly(tetra-alkoxy silane), and mixtures thereof, (B) an organo alkoxysilane selected from the group consisting of mono-organo alkoxysilane, bi-organo alkoxysilane, tri-organo alkoxysilane, and mixtures thereof, and (C) a second alkoxy silane selected from the group consisting of a poly(dialkyl)siloxane, and mixtures thereof. Preferably, the first alkoxy silane is present in an amount of 0.5 to 10% by weight of the nanoparticles, more preferably 2 to 8% by weight of the nanoparticles, and most preferably 3 to 5% by weight of the nanoparticles, including 3.5, 4, and 4.5%. Preferably, the organo alkoxysilane is present in an amount of 0.5 to 10% by weight of the nanoparticles, more preferably 1 to 6% by weight of the nanoparticles, and most preferably 1.5 to 4% by weight of the nanoparticles, including 2, 2.5, 3, and 3.5%. Preferably, the second alkoxy silane is present in an amount of 1 to 22% by weight of the nanoparticles, more preferably 3 to 18% by weight of the nanoparticles, and most preferably 7 to 15% by weight of the nanoparticles, including 7.5, 8, 8.5, 9, 9.5, 10, 10.5, 11, 11.5, 12, 12.5, 13, 13.5, 14, and 14.5%.

The first alkoxy silane may be a tetra-alkoxy silane, a poly(tetra-alkoxy silane), or mixtures thereof. Tetra-alkoxy silanes are compounds of the formula $(R^aO)_4Si$, where each $R^a$ is an organic group which may be the same or different, and each $R^a$ is preferably an alkyl groups having 1 to 20 carbon atoms, more preferably 1 to 10 carbon atoms, including 2, 3, 4, 5, 6, 7, 8, and 9 carbon atoms, including methyl, ethyl, and propyl. An example is tetraethoxy silane (TEOS). A poly(tetra-alkoxy silane) is an oligomer of one or more tetra-alkoxy silanes, formed by partial hydrolysis. Preferably the poly(tetra-alkoxy silane) contains 2 to 14 monomer units, more preferably 4 to 10 monomer units, including 5, 6, 7, 8, and 9.

The organo alkoxysilane is selected from the group consisting of mono-organo alkoxysilane, bi-organo alkoxysilane, tri-organo alkoxysilane, and mixtures thereof. The organo alkoxysilane are compounds of the formula $R^1{}_nSi(OR^b)_{4-n}$ where n is 1, 2 or 3. $R^1$ is an organic group, such as alkyl (for example, linear alkyl, branched alkyl, cyclic alkyl, glycidoxyalkyl, methancryloxyalkyl and aminoalkyl), aryl, vinyl and heteroaryl. Examples of $R^1$ include methyl, ethyl, propyl, butyl, pentyl, hexyl, heptyl, octyl, nonyl, decyl, dodecyl, tridecyl, tetradecyl, pentadecyl, hexadecyl, heptadecyl, and octadecyl. Preferably, $R^1$ contains 1 to 20 carbon atoms, more preferably 1 to 10 carbon atoms, including 2, 3, 4, 5, 6, 7, 8 and 9 carbon atoms. Each $R^b$ is an organic group which may be the same or different, and each $R^b$ is preferably an alkyl groups having 1 to 20 carbon atoms, more preferably 1 to 10 carbon atoms, including 2, 3, 4, 5, 6, 7, 8 and 9 carbon atoms, including methyl, ethyl, and propyl. An example of an organo alkoxysilane is triethoxy octylsilane.

The second alkoxy silane is selected from the group consisting of a poly(dialkyl)siloxane, and mixtures thereof. Poly(dialkyl)siloxanes are preferably oligomers of the formula $R^cO(SiR^2{}_2)(R^2{}_2SiO)_n(SiR^2{}_2)OR^c$, where n is an integer of 2 to 14, preferably 4 to 10, including 5, 6, 7, 8 and 9. Each $R^2$ is an organic group such as methyl, ethyl, or phenyl, and each $R^c$ is an end blocking group such as alkyl including methyl, ethyl, and propyl to form an alkyloxy group, or H to form a hydroxyl group; hydroxy and alkyloxy groups are both reactive groups. It is also possible that 1 to 3 of the $R^2$ groups are hydroxyl and/or alkyloxy groups. $R^2$ and $R^c$ each independently preferably contain 1 to 20 carbon atoms, more preferably 1 to 10 carbon atoms, including 2, 3, 4, 5, 6, 7, 8 and 9 carbon atoms. Preferably, the poly(dialkyl)siloxane is a polydimethylsiloxane or a polydiethylsiloxane. Preferably, the poly(dialkyl)siloxanes have a weight average molecular weight of 200 to 1400, more preferably 400 to 700.

Typically, the nanoparticles and the three components of the composition are thoroughly mixed together, and then placed into a sealed vessel. The vessel is then evacuated and heated to a temperature where at least two of components form vapor. The temperature is maintained for sufficient time to allow polymerization and formation of a coating on the nanoparticles, preferably with continuous mixing during the polymerization process. The vessel is then flooded with an inert gas stream which allows the removal of volatile by-products such as alcohols and is subsequently allowed to cool to room temperature. The polymer coating formed contains moieties of each of the three silanes: (1) silica moieties, (2) organo oxysilane moieties selected from the group consisting of mono-organo oxysilane moieties, bi-organo oxysilane moieties and tri-organo oxysilane moieties, and (3) poly(dialkyl)siloxane moieties.

Preferably, the temperature of polymerization is 80° C. to 120° C., more preferably 90° C. to 110° C., including 92, 94, 96, 98, 100, 102, 104, 106, and 108° C. Preferably the amount of time for polymerization is 0.5 to 10 hours, more preferably 1 to 6 hours, including 2, 3, 4, and 5 hours.

Silica moieties are $Si(O)_4$ groups which bond to 4 atoms, and may also be present in clusters such as $[OSi(O_2)]_nO$, where n is 2 to 14, more preferably 4 to 10, including 5, 6, 7, 8 and 9. Organo oxysilane moieties are $R^1{}_nSi(O)_{4-n}$ groups which bond to "4-n" other atoms, with n an integer of 1, 2 or 3. $R^1$ is an organic group, such as alkyl (for example, linear alkyl, branched alkyl, cyclic alkyl, glycidoxyalkyl, methancryloxyalkyl and aminoalkyl), aryl, vinyl and heteroaryl. Examples of $R^1$ include methyl, ethyl, propyl, butyl, pentyl, hexyl, heptyl, octyl, nonyl, decyl, dodecyl, tridecyl, tetradecyl, pentadecyl, hexadecyl, heptadecyl, and octadecyl. Preferably, $R^1$ contains 1 to 20 carbon atoms, more preferably 1 to 10 carbon atoms, including 2, 3, 4, 5, 6, 7, 8 and 9 carbon atoms. An example of an organo oxysilane moiety is octylsilane.

Poly(dialkyl)siloxane moieties are $O(SiR^2{}_2)(R^2{}_2SiO)_n(SiR^2{}_2)O$ or $O(SiR^2{}_2)(R^2{}_2SiO)_n(SiR^2{}_2)OR^e$ groups which bond to other atoms, where n is an integer of 2 to 14, preferably 4 to 10, including 5, 6, 7, 8, and 9. Each $R^2$ is independently an organic group such as methyl, ethyl, or phenyl, and each $R^e$ is an end blocking groups such as alkyl including methyl, ethyl, and propyl to form an alkyloxy group, or H to form a hydroxyl group; hydroxy and alkyloxy groups are both reactive groups. It is also possible that 1 to 3 of the $R^2$ groups are hydroxyl and/or alkyloxy groups. $R^2$ and $R^e$ each independently preferably contain 1 to 20 carbon atoms, more preferably 1 to 10 carbon atoms, including 2, 3, 4, 5, 6, 7, 8, and 9 carbon atoms. Preferably, the poly(dialkyl)siloxane moiety is a polydimethylsiloxane moiety or a polydiethylsiloxane moiety.

A variety of techniques are available to analyze the coated powder of the present invention. The inorganic oxide particles may be dissolved with various acids, determining the relative amount of polymer and inorganic oxide, and then the remaining polymer coating may be examined using FTIR (Fourier Transform Infrared Spectroscopy) to determine the presence of different moieties and the relative amounts of each moiety. Other techniques, such as mass spectrometry, TGA (Thermogravimetric Analysis), or ICP (Inductively Coupled Plasma Spectroscopy) may also be used to establish relative monomer unit ratios. A baseline may be established by using a standard of known composition.

The coated powder may also be analyzed by solid state NMR, examining $^{13}C$ and $^{29}Si$ NMR signals to determine the presence of different moieties and the relative amounts of each moiety. Furthermore, the inorganic oxide particles may be dissolved with various acids, and the remaining polymer coating may be analyzed by NMR, examining $^{13}C$ and $^{29}Si$ NMR signals to determine the presence of different moieties and the relative amounts of each moiety. A baseline may be established by using a standard of known composition.

The coated powders may be examined for properties using the photostability test, the chemical reactivity test and the hydrophobicity test. Preferably, the coated powders have a photostability of $\Delta E=0$ to 7, more preferably $\Delta E=0$ to 5, most preferably $\Delta E=0, 1, 2, 3$ or 4. Preferably, the coated powders have a chemical reactivity of $\Delta E=0$ to 20, more preferably $\Delta E=0$ to 17, most preferably $\Delta E=0, 1, 2, 3, 4, 5, 6, 7, 8, 9, 10, 11, 12, 13, 14, 15$, or 16. Preferably the coated powders are hydrophobic or marginally hydrophobic, most preferably hydrophobic.

The coated powder may be used to form dispersions with non-polar liquids, preferably cosmetic oils, such as capric/caprylic triglycerides, linear alkyl benzoate, ethylhexyl benzoate, natural product oils, and silicone oils. Preferably, the dispersions contain at least 40% by weight coated powder (solids), more preferably at least 50% by weight coated powder (solids), including at least 55% by weight coated powder (solids), at least 60% by weight coated powder (solids), and at least 65% by weight coated powder (solids), such as 50-65% by weight coated powder (solids), and 55-60% by weight coated powder (solids). Such dispersions may be made by a variety of conventional mixing processes, including mixing with a rotor-stator machine, planetary mixing, high-pressure homogenizers, ultra-sonic mixing, and media milling. An adjunct emulsifier or dispersant may be included in the dispersions. Examples include triceteareth-4 phosphate (Hostaphat KW 340 D; Clariant) at 5-15% by weight of solids.

Surprisingly, high solids dispersions of the coated powders have relatively low viscosity. Preferably, the viscosity is at most 60,000 cP, more preferably at most 30,000 cP, most preferably at most 6,000 cP. Examples include a viscosity of 1,000 to 50,000 cP, and 5,000 to 30,000 cP.

The coated powder, as well as the dispersions of the coated powder may be used in a variety of products. They may be added to dermatological compositions to provide UV protection to skin, especially in the case of $TiO_2$ and ZnO containing coated powders; the coated powder may also be added to such compositions as inorganic pigments. The coated powders may also be added to shampoos, lotions, gels, hairsprays, aerosol foam creams or emulsions, for washing, coloring and for styling hair, while also providing UV protection to hair. They may be added to paints, sealants and other coatings for wood, plastics and other construction materials; again, UV protection is provided in the case of $TiO_2$ and ZnO containing coated powders. They may also be added to resins, filled polymers and plastics, and inks. Magnetic fluids may be prepared when the metal oxide is magnetic, as in the case of certain iron oxides and rare-earth oxides.

Cosmetic and dermatological preparations may include cosmetic ingredients, auxiliaries and/or additives, for example, co-emulsifiers, fats and waxes, stabilizers, thickeners, biogenic active ingredients, film formers, fragrances, dyes, pearlizing agents, preservatives, pigments, electrolytes, and pH regulators. Suitable co-emulsifiers are, preferably, known W/O and also O/W emulsifiers, for example, polyglycerol esters, sorbitan esters or partially esterified glycerides. Typical examples of fats are glycerides; waxes such as beeswax, paraffin wax or microcrystalline waxes, optionally in combination with hydrophilic waxes. Stabilizers including metal salts of fatty acids, for example, magnesium, aluminum and/or zinc stearate. Examples of thickeners include crosslinked polyacrylic acids and derivatives thereof, polysaccharides, such as xanthan gum, guar gum, agar, alginates and tyloses, carboxymethylcellulose and hydroxyethylcellulose, and fatty alcohols, monoglycerides and fatty acids, polyacrylates, polyvinyl alcohol and polyvinylpyrrolidone. Biogenic active ingredients include plant extracts, protein hydrolyzates and vitamin complexes. Customary film formers include, for example, hydrocolloids, such as chitosan, microcrystalline chitosan or quaternary chitosan, polyvinylpyrrolidone, vinylpyrrolidone/vinyl acetate copolymers, polymers of the acrylic acid series, and quaternary cellulose derivatives. Examples of preservatives include parabens, diazolidinyl urea, iodopropynyl butylcarbamate, and sorbic acid. Examples of pearlizing agents include glycol distearic esters, such as ethylene glycol distearate, fatty acids and fatty acid monoglycol esters. Dyes which may be used are the substances suitable and approved for cosmetic purposes. Antioxidants, such as amino acids, retinol, flavonoids, polyphenols, vitamin C and tocopherols, may also be included.

The cosmetic and dermatological preparations may be in the form of a solution, dispersion or emulsions; for example sunscreen preparations may be in liquid, paste or solid form, for example as water-in-oil creams, oil-in-water creams and lotions, aerosol foam creams, gels, oils, marking pencils, powders, sprays or alcohol-aqueous lotions. Solvents for these compositions include water; oils, such as triglycerides of capric acid or of caprylic acid, as well as castor oil; fats, waxes and other natural and synthetic fatty substances, esters of fatty acids with alcohols of low carbon number, for example with isopropanol, propylene glycol or glycerol, or esters of fatty alcohols with alkanoic acids of low carbon number or with fatty acids; alcohols, diols or polyols of low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether. Other examples include isopropyl myristate, isopropyl palmitate, isopropyl stearate, isopropyl oleate, n-butyl stearate, diisopropyl adipate, n-hexyl laurate, n-decyl oleate, glyceryl stearate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, and erucyl erucate.

The cosmetic and dermatological preparations may be in the form of solid sticks, and may include natural or synthetic waxes, fatty alcohols or fatty acid esters, liquid oils for example paraffin oils, castor oil, isopropyl myristate, semi-solid constituents for example petroleum jelly, lanolin, solid constituents such as beeswax, ceresine and microcrystalline waxes and ozocerite, and high-melting waxes including carnauba wax and candelilla wax.

Cosmetic preparations may be in the form of gels and preferably include water, organic thickeners, for example gum arabic, xanthan gum, sodium alginate, cellulose derivatives such as methylcellulose, hydroxymethylcellulose, hydroxyethylcellulose, hydroxypropylcellulose, hydroxpropylmethylcellulose and inorganic thickeners, such as aluminum silicates, for example, bentonites, or a mixture of polyethylene glycol and polyethylene glycol stearate or distearate.

The coated powders and dispersions may also be included in paints, sealants and other coatings, which may also contain binders such as polyacrylates, polyurethanes, polyalkyds, polyepoxides, polysiloxanes, polyacrylonitriles and/or polyesters. Organic solvents may also be present, including ethanol, butyl acetate, ethyl acetate, acetone, butanol, alkanes, methanol, propanol, and pentanol; ethers/acetals such as tetrahydrofuran and 1,4-dioxane; ketones such as diacetone alcohol, and methyl ethyl ketone; and polyhydric alcohol derivatives such as ethylene glycol, propylene glycol, and diethylene glycol or mixtures thereof. These compositions may be used to coat a variety of substrates, including wood, PVC (polyvinyl chloride), plastic, steel, aluminum, zinc, copper, MDF (medium density fiberboard), glass and concrete. Depending on which coated powders are included, the compositions provide the substrate with a coating that may be transparent, UV-resistant, and/or provide greater scratch resistance.

The coated powder and dispersions may be blended with a resin, to provide an organic polymer composite. Examples of resins include, polyethylene, polypropylene, polystyrene, polyethylene terephthalate, AS (acrylonitrile styrene) resins, ABS (acrylonitrile butadiene styrene) resins, AES (acrylonitrile ethylene styrene) resins, polyvinylidene chloride, methacrylic resins, polyvinyl chloride, polyamides, polycarbonates, polyallyl esters, polyimides, polyacetals, polyether ketones, polyether sulfones, polyphenyl oxides and polyphenylene sulfides, as well as mixtures thereof. Also present in these compositions may be coloring agents, fluorescent agents, and additives, such as antioxidants, anti-aging agents, UV-absorbers, lubricants, antistatic agents, surfactants, fillers (the coated powder and dispersions may also act as fillers), plasticizers, stabilizers, blowing agents, expanding agents, electroconductive powder, electroconductive short fiber, deodorizing agents, softening agents, thickeners, viscosity-reducing agents, diluents, water-repellent agents, oil-repellent agents, cross-linking agents and curing agents. These organic polymer compositions may be shaped by a variety of techniques, including injection molding, blow molding, extrusion molding, calender molding, flow molding, compression molding, melt-blown molding, and the spun bond method, whereby shape-imparted products such as fiber, thread, film, sheets, tapes, and injection-molded products and shaped bodies such as hollow thread, pipes, and bottles may be produced. Alternatively, the compositions can be subjected to secondary molding methods generally applied to thermoplastic resins such as vacuum forming, air pressure forming, and laminate molding.

EXAMPLES

Example 1

This Example illustrates a coated nanocrystalline $TiO_2$ powder of the present invention. A 10.0 g charge of nanocrystalline $TiO_2$ (specific surface area=45 $m^2/g$, corresponding average particle size=32 nm, P25S; Evonik) is loaded into a laboratory blender together with a mixture of tetraethoxy silane (0.4 g), triethoxy octylsilane (0.3 g) and hydroxy terminated polydimethylsiloxane (0.95 g). The mixture is homogenized for 30 seconds and then transferred to a glass container which is subsequently sealed. The sealed container is then transferred to an oven where it is heated to a temperature of 90° C. and held for 4 hours. The resultant coated powder is then dried by unsealing the container and returning the container to the same oven where it is held at a temperature of 100-110° C. and held for 1.5 hours. The resultant coated powder is highly hydrophobic, passes the n-propyl gallate test ($\Delta E=16.74$) and passes the photostability test ($\Delta E=3.65$). A 50% solids dispersion in ethylhexyl benzoate is highly pourable and fluid showing a run-off distance of 128 mm.

Example 2

This Comparative Example illustrates a coated nanocrystalline $TiO_2$ powder outside the scope of the present invention. A 10.0 g charge of nanocrystalline $TiO_2$ (specific surface area=45 $m^2/g$, corresponding average particle size=32 nm, P25S; Evonik) is loaded into a laboratory blender together with a mixture of tetraethoxy silane (0.4 g) and hydroxy terminated polydimethylsiloxane (1.2 g). The mixture is homogenized for 30 seconds and then transferred to a glass container which is subsequently sealed. The sealed container is then transferred to an oven where it is heated to a temperature of 100° C. and held for 2 hours. The resultant coated powder is then dried by unsealing the container and returning the container to the same oven where it is held at a temperature of 100-110° C. and held for 1.5 hours. The resultant coated powder is hydrophobic, fails the n-propyl gallate test ($\Delta E=24.18$), and passes the photostability test ($\Delta E=5.92$). A 50% solids dispersion in ethylhexyl benzoate displays poor fluidity showing a run-off distance of 84 mm. The dispersion behavior and chemical reactivity of this coated powder render it unsuitable for commercial use.

Example 3

This Comparative Example illustrates a coated nanocrystalline $TiO_2$ powder outside the scope of the present invention. A 10.0 g charge of nanocrystalline $TiO_2$ (specific surface area=45 $m^2/g$, corresponding average particle size=32 nm, P25S; Evonik) is loaded into a laboratory blender together with a mixture of triethoxy octylsilane (0.4 g) and hydroxy terminated polydimethylsiloxane (1.6 g). The mixture is homogenized for 30 seconds and then transferred to a glass container which is subsequently sealed. The sealed container is then transferred to an oven where it is heated to a temperature of 100° C. and held for 2 hours. The resultant coated powder is then dried by unsealing the container and returning the container to the same oven where it is held at a temperature of 100-110° C. and held for 1.5 hours. The resultant coated powder is hydrophobic, and displays good fluidity at 50% solids in ethylhexyl benzoate but fails the photostability test ($\Delta E=11.47$), making it unsuitable for commercial use.

Example 4

This Comparative Example illustrates a coated nanocrystalline $TiO_2$ powder outside the scope of the present invention. A 10.0 g charge of nanocrystalline $TiO_2$ (specific surface area=45 $m^2/g$, corresponding average particle size=32 nm, P25S; Evonik) is loaded into a laboratory blender together with a mixture of tetraethoxy silane (0.2 g) and), triethoxy octylsilane (0.8 g). The mixture is homogenized for 30 seconds and then transferred to a glass container which is subsequently sealed. The sealed container is then transferred to an oven where it is heated to a temperature of 100° C. and held for 2 hours. The resultant coated powder is then dried by unsealing the container and returning the container to the same oven where it is held at a temperature of 100-110° C. and held for 1.5 hours. The resultant coated powder is hydrophobic, but displays poor fluidity and forms a paste at only 40% solids in ethylhexyl benzoate making it unsuitable for commercial use.

Example 5

This Comparative Example illustrates the properties of commercially available $TiO_2$ nanopowders that are outside the scope of the present invention.

| Test | T-Cote 031 (Sensient) | Aeroxide T-805 031 (Evonik) | Aeroxide P25S (Evonik) |
|---|---|---|---|
| Coating | Poly dialkyl siloxane | Octyl silane | None |
| Hydrophobicity | Fail | Pass | Fail |
| Photostability ($\Delta E$ at 15 min) | Fail 12.29 | Pass 7.69 | Fail 15.44 |
| Chemical Reactivity (n-Propyl Gallate Test) | Fail 31.64 | Pass 20.17 | Fail 37.42 |
| Pourability (50% Solids in ethylhexyl benzoate) | Pass (Highly Fluid) | Fail (Thick Paste) | Fail (Thick Paste) |
| Run-off distance | 235 mm | 2 mm | 0 mm |

This Comparative Example illustrates that each of the commercially available $TiO_2$ nanopowders possesses at least one undesirable property for use in commercial application.

Example 6

This Example illustrates a high solids dispersion of the present invention that is suitable for addition to cosmetic formulations. 460 g of Ethylhexyl benzoate (Finsolv® EB; Innospec) and 40 g of an emulsifier are added to a jacketed steel container which is maintained at a constant temperature of 30° C. The emulsifier, triceteareth-4 phosphate (Hostaphat KW 340 D; Clariant) is a waxy solid, anionic O/W emulsifier designed to be used in formulations requiring some level of viscosity such as cream preparations. The contents of the vessel are pre-mixed using a Cowels saw-tooth high shear impeller under mild mixing conditions for 5 minutes until the mixture is homogeneous. In the configuration used in this example, the impeller blade diameter is ⅓ of the vessel diameter and is placed 1 blade diameter from the bottom of the vessel. 500 g of the coated $TiO_2$ nanopowder of Example 1 is added to the liquid contents under mild mixing until all the powder is wetted. The mixer speed is then increased to 2500 rpm for 15 minutes. The resultant dispersion is pourable and has a viscosity of 4600 cP.

Example 7

This Example illustrates a coated nanocrystalline ZnO powder of the present invention. A 10 g charge of nanocrystalline ZnO (specific surface area=17 $m^2/g$, corresponding average particle size=63 nm) is loaded into a laboratory blender together with a 1.0 g mixture of tetraethoxy silane, triethoxy octylsilane and hydroxy terminated polydimethylsiloxane in the same relative proportions as in Example 1. The mixture is homogenized for 30 seconds and then transferred to a glass container which is subsequently sealed. The sealed container is then transferred to an oven where it is heated to a temperature of 100-110° C. and held for 1.5 hours. The resultant coated powder is then dried by unsealing the container and returning the container to the same oven where it is held at a temperature of 100-110° C. and held for 1.5 hours. The resultant coated powder is highly hydrophobic and passes the photoactivity test using DPPH as the indicator dye. The coated powder of this Example can be dispersed at 65% solids in capric/caprylic triglycerides (ALDO® MCT Special KFG, Lonza, CAS Number 73398-61-5), ethylhexyl benzoate (Finsolv® EB, Innospec), and linear alkyl benzoate (Finsolv® TN $C_{12-15}$ Alkyl Benzoate CAS No.: 68411-27-8) to yield pourable dispersions having viscosities below 10,000 cP. The coated powder of this example and corresponding dispersions are suitable for use in cosmetic sunscreen formulations.

Example 8

This Example illustrates a coated nanocrystalline $Fe_2O_3$ powder of the present invention. A 10 g charge of nanocrystalline $\gamma$-$Fe_2O_3$ (specific surface area=38 $m^2/g$, corresponding average particle size=30 nm) is loaded into a laboratory blender together with a 1.5 g mixture of tetraethoxy silane, triethoxy octylsilane and hydroxy terminated polydimethylsiloxane in the same relative proportions as in Example 1. The mixture is homogenized for 30 seconds and then transferred to a glass container which is subsequently sealed. The sealed container is then transferred to an oven where it is heated to a temperature of 100-110° C. and held for 1.5 hours. The resultant coated powder is then dried by unsealing the container and returning the container to the same oven where it is held at a temperature of 100-110° C. and held for 1.5 hours. The resultant coated powder is highly hydrophobic. The coated powder of this example can be dispersed at 50% solids in ethylhexyl benzoate (Finsolv® EB, Innospec) to yield a pourable dispersion having a viscosity below 3,000 cP. The coated powder of this example is suitable for use in cosmetic preparations, ferrofluids, and magneto-rheological fluids.

Example 9

Prophetic

This Example illustrates a water-in-oil emulsion cosmetic sunscreen preparation of the present invention containing only inorganic UV screening agents.

The following oil-phase ingredients are added to a heated vessel and mixed at low intensity at 80° C. until clear.

| Ingredients | Parts by Weight |
|---|---|
| Emulsifier (Abil EM-90: Bis-PEG/PPG Dimethicone, Cyclopentasiloxane; Evonik-Goldschmidt GmbH) | 5.0 |
| 2-Ethylhexyl Palmitate (CAS# 29806-73-3, Crodamol OP; Croda Ltd.) | 11.0 |
| Decamethylcyclopentasiloxane (245 Silicone Oil; Dow Corning) | 7.5 |
| Cetyl Dimethicone (Abil Wax 9801; Evonik-Goldschmidt GmbH) | 3.0 |
| White Mineral Oil (Carnation Oil; Sonneborn) | 2.0 |
| Emollient White Ceresine Wax (Ceresine Sp-252; Strahl & Pitsch) | 1.0 |
| Emollient (Castorwax MP70 Hydrogenated Castor Oil; Vertellus) | 0.5 |

The oil-phase mixture is then cooled to 60° C. and mixed with the coated $TiO_2$ powder of Example 1 (12.0 parts by weight) and subsequently passed through a media mill until the mixture is homogeneous. This mixture is then cooled to 45° C.

The following water-phase ingredients are combined in a separate vessel.

| Ingredients | Parts by Weight |
|---|---|
| Deionized water | 56.5 |
| Preservative (Germaben II; ISP) | 1.0 |
| Sodium Chloride | 0.5 |

The milled oil-phase mixture and the water phase mixture are mixed until a homogeneous emulsion is formed. Note that optional fragrance (0.2 parts by weight) may be substituted for the equivalent amount of deionized water.

Example 10

Prophetic

This Example illustrates a water-in-oil emulsion cosmetic sunscreen preparation of the present invention containing a combination of organic and inorganic UV screening agents. This example shows that the high solids dispersions of the present invention can be used to avoid time consuming milling operations typical in the manufacture of commercial topical sunscreens containing inorganic UV screening agents.

The following oil-phase ingredients are added to a heated vessel and mixed at low intensity at 80° C. until homogeneous and subsequently cooled to 45° C.

| Ingredients | Parts by Weight |
|---|---|
| Emulsifier (Abil EM-90: Bis-PEG/PPG Dimethicone, Cyclopentasiloxane; Evonik-Goldschmidt GmbH) | 5.0 |
| Ethylhexyl benzoate (Finsolv ® EB; Innospec) | 4.0 |
| 50% Solids $TiO_2$ dispersion in Ethylhexyl benzoate (Finsolv ® EB; Innospec) of Example 1 | 12.0 |
| 65% Solids ZnO dispersion in Ethylhexyl benzoate (Finsolv ® EB; Innospec) of Example 7 | 9.0 |
| Decamethylcyclopentasiloxane (245 Silicone Oil; Dow Corning) | 7.5 |
| Octylmethyl Cinnamate | 5.0 |
| Octocrylene | 7.0 |

-continued

| Ingredients | Parts by Weight |
|---|---|
| Cetyl Dimethicone (Abil Wax 9801; Evonik-Goldschmidt GmbH) | 3.0 |
| White Mineral Oil (Carnation Oil; Sonneborn) | 2.0 |
| Emollient White Ceresine Wax (Ceresine Sp-252; Strahl & Pitsch) | 1.0 |
| Emollient (Castorwax MP70 Hydrogenated Castor Oil; Vertellus) | 0.5 |

The following water-phase ingredients are combined in a separate vessel.

| Ingredients | Parts by Weight |
|---|---|
| Deionized water | 40.5 |
| Propylene Glycol, USP | 2.0 |
| Preservative (Germaben II; ISP) | 1.0 |
| Sodium Chloride | 0.4 |
| Sodium EDTA | 0.1 |

The oil-phase mixture and the water phase mixture are mixed until a homogeneous emulsion is formed. Note that optional fragrance (0.2 parts by weight) may be substituted for the equivalent amount of deionized water.

Example 11

Prophetic

This Example illustrates a plastic composition of the present invention. The coated $TiO_2$ nanopowder of Example 1 (2.0% by weight) is mixed with linear low density polyethylene (Petrothene NA940 Film Extrusion Grade; LDPE; Lyondell) (98% by weight) in a twin screw extruder at temperatures ranging from 165° C.-220° C., with 185° C. being typical. The resultant UV stabilized plastic is suitable for extrusion into a master-batch or into films or finished articles. Adjunct components such as colorants, slip/antiblock agents, thermal stabilizers and the like can be added to the composition as required by the specific application.

Example 12

Prophetic

This Example illustrates an example of a UV curable coating composition of the present invention. The following ingredients are mixed until homogeneous.

| Ingredients | Parts by Weight |
|---|---|
| Bisphenol A epoxy acrylate 80% in neopentylglycol propoxylatediacrylate | 44.0 |
| Propoxylated neopentyl glycol diacrylate | 30.9 |
| Ditrimethylolpropane tetraacrylate | 3.2 |
| Benzophenone | 6.0 |
| Acrylated amine synergist (Chivacure OPD; Campbell and Co.) | 9.9 |
| Photoinitiator (Irgacure 184; BASF) | 2.0 |
| Rheology modifier (Bentone 27; Elementis Specialties) | 0.4 |
| Coated $TiO_2$ nanopowder of Example 1 | 3.6 |

The composition of this example can be applied as a wet film to a substrate using a wire-wound rod or spray gun and subsequently cured using UV radiation to yield a UV protective hardcoat.

REFERENCES

EP 0761774
GB 785,393
GB 825,404
US 20060167138
US 20060210495
U.S. Pat. No. 3,024,126
U.S. Pat. No. 3,562,153
U.S. Pat. No. 3,647,742
U.S. Pat. No. 3,649,588
U.S. Pat. No. 3,920,865
U.S. Pat. No. 3,948,676
U.S. Pat. No. 4,061,503
U.S. Pat. No. 4,061,503
U.S. Pat. No. 4,068,024
U.S. Pat. No. 4,141,751
U.S. Pat. No. 4,233,366
U.S. Pat. No. 4,454,288
U.S. Pat. No. 4,644,077
U.S. Pat. No. 4,882,225
U.S. Pat. No. 5,277,888
U.S. Pat. No. 5,486,631
U.S. Pat. No. 5,536,492
U.S. Pat. No. 5,562,897
U.S. Pat. No. 5,565,591
U.S. Pat. No. 5,607,994
U.S. Pat. No. 5,631,310
U.S. Pat. No. 5,718,907
U.S. Pat. No. 5,756,788
U.S. Pat. No. 5,843,525
U.S. Pat. No. 5,959,004
U.S. Pat. No. 5,993,967
U.S. Pat. No. 6,022,404
U.S. Pat. No. 6,045,650
U.S. Pat. No. 6,086,668
U.S. Pat. No. 6,214,106
U.S. Pat. No. 6,500,415
U.S. Pat. No. 7,182,938
U.S. Pat. No. 7,438,836
WO 2009/131910
WO 95/23192

What is claimed is:

1. A coated powder comprising:
    (a) nanoparticles, and
    (b) a coating, on the surface of the nanoparticles, comprising
        (1) silica moieties,
        (2) organo oxysilane moieties selected from the group consisting of mono-organo oxysilane moieties, bi-organo oxysilane moieties and tri-organo oxysilane moieties, and
        (3) poly(dialkyl)siloxane moieties,
    wherein the coated powder is photostable, not chemically reactive, passes the hydrophobicity test, and is pourable,
    wherein pourable means that a dispersion comprising 50 wt % coated powder, 5 wt % triceteareth-4 phosphate and ethylhexyl benzoate shows a run-off distance exceeding 100 mm.

2. The coated powder of claim 1, wherein the nanoparticles comprise at least one oxide selected from the group consisting of zinc oxides, titanium oxides, silicon oxides, aluminum oxides, iron oxides, bismuth oxides, tin oxides, indium oxides tungsten oxides and rare-earth metal oxides.

3. The coated powder of claim 2, wherein the nanoparticles comprise at least one oxide selected from the group consisting of ZnO, $TiO_2$, $SiO_2$, $Al_2O_3$, $Fe_2O_3$, $CeO_2Bi_2O_3$, antimony-tin oxide, indium-tin oxide, doped $WO_3$, and mixtures thereof.

4. The coated powder of claim 1, wherein the nanoparticles have an average particle size of 10-500 nm.

5. The coated powder of claim 1, wherein the nanoparticles have an average particle size of 15-150 nm.

6. The coated powder of claim 1, wherein the organo oxysilane moieties each have the formula $R^1{}_nSiO_{4-n}$, with n=1, 2 or 3, and each $R^1$ group is independently selected from the group consisting of alkyl, alkenyl, alkynyl, aryl and heterocyclic radical.

7. The coated powder of claim 6, wherein each $R^1$ group has 1-18 carbon atoms and is independently selected from the group consisting of alkyl, alkenyl and aryl.

8. The coated powder of claim 7, wherein each $R^1$ group is independently selected from the group consisting alkyl, aryl, vinyl, glycidoxyalkyl, methacryloxyalkyl, aminoalkyl and mercaptoalkyl.

9. The coated powder of claim 1, wherein the poly(dialkyl) siloxane moieties each have the formula $O(SiR^2{}_2)(R^2{}_2SiO)_n(SiR^2{}_2)O$ or $O(SiR^2{}_2)(R^2{}_2SiO)_n(SiR^2{}_2)OR^c$, where n is an integer of 2 to 14, each $R^2$ group is an alkyl, and $R^c$ is selected from the group consisting of H, methyl, ethyl and propyl.

10. The coated powder of claim 1, wherein the poly(dialkyl) siloxane moieties are polydimethyl siloxane moieties or polydiethyl siloxane moieties.

11. The coated powder of claim 1, wherein the silica moieties are present in an amount of 0.5-10% of the weight of the nanoparticle.

12. A dispersion, comprising the coated powder of claim 1, and a liquid carrier.

13. The dispersion of claim 12, comprising at least 50% by weight of the coated powder,
    wherein the dispersion shows a run-off distance exceeding 100 mm.

14. The dispersion of claim 12, wherein the dispersion has a viscosity of at most 10,000 cP when measured at 25° C. at shear rates ranging from 0.1 $sec^{-1}$ to 100 $sec^{-1}$.

15. A composition comprising the coated powder of claim 1, wherein the composition is a paint, stain, coating or ink.

16. The coated powder of claim 1, wherein the silica moieties are present in an amount of 0.5 to 10% by weight of the nanoparticles;
    the organo oxysilane moieties are present in an amount of 0.5 to 10% by weight of the nanoparticles; and
    the poly(dialkyl)siloxane moieties are present in an amount of 1 to 22% by weight of the nanoparticles.

17. The coated powder of claim 1, wherein the organo alkoxysilane moieties are octylsilane moieties and the poly(dialkyl)siloxane moieties are polydimethylsiloxane moieties or polydiethylsiloxane moieties.

18. The coated powder of claim 1, wherein the silica moieties are $Si(O)_4$ groups or $[OSi(O_2)]_nO$ clusters where n is 2 to 14;
    the organo alkoxysilane moieties are $R^1{}_nSi(O)_{4-n}$ groups where n is an integer of 1, 2, or 3 and $R^1$ is an organic group containing 1 to 20 carbon atoms; and
    the poly(dialkyl)siloxane moieties are $O(SiR^2{}_2)(R^2{}_2SiO)_n(SiR^2{}_2)O$ or $O(SiR^2{}_2)(R^2{}_2SiO)_n(SiR^2{}_2)OR^c$ groups where n is an integer of 2 to 14, $R^2$ is an organic group containing 1 to 20 carbon atoms, and $R^c$ is an end-blocking group containing 1 to 20 carbon atoms.

19. A method of protecting skin from UV light, comprising coating skin with a composition comprising the coated powder of claim 1.

20. A method of protecting skin from UV light, comprising coating skin with the dispersion of claim 12.

* * * * *

UNITED STATES PATENT AND TRADEMARK OFFICE
CERTIFICATE OF CORRECTION

| | | |
|---|---|---|
| PATENT NO. | : 9,139,737 B1 | Page 1 of 1 |
| APPLICATION NO. | : 13/301628 | |
| DATED | : September 22, 2015 | |
| INVENTOR(S) | : Kushal D. Shah et al. | |

It is certified that error appears in the above-identified patent and that said Letters Patent is hereby corrected as shown below:

Title Page

Page 2, References Cited (56)

Column 2, line 3, please delete "surkefaces"" and insert --surfaces"--

In the Claims

Column 18, line 2, please delete "indium oxides" and insert --indium oxides,--

Column 18, line 23, please delete "consisting alkyl," and insert --consisting of alkyl,--

Column 18, line 56, please delete "alkoxysilane" and insert --oxysilane--

Column 18, line 62, please delete "alkoxysilane" and insert --oxysilane--

Signed and Sealed this
Sixteenth Day of February, 2016

Michelle K. Lee
*Director of the United States Patent and Trademark Office*